US011061012B2

(12) United States Patent
Dzenis (10) Patent No.: US 11,061,012 B2
(45) Date of Patent: Jul. 13, 2021

(54) METHOD FOR DETERMINING QUALITY OR EVOLVEMENT OF A PHYSICAL PROPERTY OF A VISCOUS SUBSTANCE

(71) Applicant: Gunars Dzenis, Peachtree City, GA (US)

(72) Inventor: Gunars Dzenis, Peachtree City, GA (US)

( * ) Notice: Subject to any disclaimer, the term of this patent is extended or adjusted under 35 U.S.C. 154(b) by 0 days.

(21) Appl. No.: 16/569,396

(22) Filed: Sep. 12, 2019

(65) Prior Publication Data

US 2021/0080447 A1   Mar. 18, 2021

(51) Int. Cl.
| | | |
|---|---|---|
| *G01N 33/38* | (2006.01) | |
| *G01N 25/58* | (2006.01) | |
| *H04W 4/80* | (2018.01) | |
| *G06K 7/10* | (2006.01) | |

(52) U.S. Cl.
CPC ........... *G01N 33/383* (2013.01); *G01N 25/58* (2013.01); *G06K 7/10128* (2013.01); *G06K 7/10158* (2013.01); *H04W 4/80* (2018.02)

(58) Field of Classification Search
CPC ...... G01N 33/383; G01N 19/00; G01N 25/58; G06K 7/10158; H04W 4/80
USPC .................. 340/10.1–10.5; 700/265; 366/59; 706/12
See application file for complete search history.

(56) References Cited

U.S. PATENT DOCUMENTS

| | | | |
|---|---|---|---|
| 4,186,592 A |  | 2/1980 | Eirich et al. |
| 5,541,855 A | * | 7/1996 | Enzler ................... G01N 11/14 366/142 |
| 6,045,730 A | * | 4/2000 | Potter ..................... B28B 11/24 156/346 |
| 6,779,385 B2 | * | 8/2004 | Belanger ............ G01N 33/2847 73/73 |
| 7,231,815 B2 |  | 6/2007 | Kanare |
| 7,289,916 B2 | * | 10/2007 | Drnevich ................ C04B 28/02 702/138 |
| 7,384,180 B2 | * | 6/2008 | Jarvinen .............. G01N 33/383 366/2 |
| 7,398,131 B2 |  | 7/2008 | Trost et al. |
| 7,457,785 B1 | * | 11/2008 | Greitzer ................... G01D 1/18 706/12 |
| 7,681,438 B2 |  | 3/2010 | Albadri et al. |

(Continued)

*Primary Examiner* — Nam V Nguyen
(74) *Attorney, Agent, or Firm* — Michael J. Bootcheck, LLC; Michael J. Bootcheck (57) ABSTRACT

The inventive concept relates to a method of determining the relative ratios or percentages of certain characteristics or properties of viscous substances, wherein moisture content is a key determinant. The method utilizes placement of passive Radio Frequency Identification (RFID) instrumentation into a slurry or existing viscous mixture of substances. The RFID then reads moisture and/or other physical properties of the substance, typically process parameters such as temperature and/or pH. The readings are queried using an interrogator to acquire the data wirelessly. As a planning step, it is necessary to correlate the data with a variety of specially-developed algorithms specific to a viscous mixture associated with a particular process. The acquired readings will then provide a user with instantaneous information which will be determinative of the degree of completeness or maintenance of a certain property of the process.

19 Claims, 5 Drawing Sheets

(56) References Cited

U.S. PATENT DOCUMENTS

| | | | |
|---|---|---|---|
| 8,818,561 B2* | 8/2014 | Koehler | G01N 11/00 |
| | | | 700/265 |
| 9,032,791 B2 | 5/2015 | Duncan | |
| 9,511,510 B2* | 12/2016 | Roy | B28C 7/02 |
| 9,964,942 B2* | 5/2018 | Nelson | G05B 19/402 |
| 10,276,015 B2 | 4/2019 | Lang et al. | |
| 2001/0017053 A1* | 8/2001 | Rynhart | G01N 27/223 |
| | | | 73/73 |
| 2007/0126433 A1 | 6/2007 | Theophanous et al. | |
| 2017/0248475 A1* | 8/2017 | Bonifas | G06K 7/10158 |

* cited by examiner

Fig. 4B

Figure 4 - Algorithm

METHOD FOR DETERMINING QUALITY OR EVOLVEMENT OF A PHYSICAL PROPERTY OF A VISCOUS SUBSTANCE

CROSS-REFERENCES TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

BACKGROUND OF THE INVENTION

(1) Field of the Invention

The field of the present inventive concept relates generally to methods and equipment utilized to monitor and measure the progression, or phase, of at least one physical property of a viscous substance, as the substance undergoes an industrial or commercial process. The process itself may concern the curing, reactivity, maintenance, or transport of a viscous mixture, such as concrete, asphalt, and other types of materials which at some point, exist in a slurry condition.

Conversely, the opposite is true, in that situations exist wherein substances must be converted to, maintained in, or terminate in, a slurry state at some point in a particular process. In this instance, the progression of the substance during the process may be measured by the inventive concept disclosed. Basically, any system that utilizes solid-liquid substance combinations which require measurement of moisture content could benefit from the technology disclosed herein. For example, slurry transport systems that transport minerals frequently accomplish this by use of a pipeline in which a liquid is added to facilitate transporting the mineral long distances in a slurry state. At the terminus of the slurry pipeline, the mineral is then extracted from the slurry.

As mentioned above, there are many processes in which the control of moisture content plays an important variable. In most cases, it is difficult or very expensive to measure the moisture content and therefore it is rarely done. As a substantial improvement to these processes, the method disclosed herein effectively and accurately measures certain physical properties of the viscous substance, including, but not limited to, moisture content, density, specific gravity, thermal conductivity, electrical conductivity, hardness, strength, and ductility.

By way of further example, concrete production involves reacting several ingredients, to include water, aggregate, cement, and other additives. The concrete is made as a viscous fluid, placed into a form to provide a desired shape, and then the exothermic process is allowed to occur. During the exothermic process, temperature and moisture content play a key role in the proper curing process to develop the desired compressive strength. Current methods of determining the cure rate of concrete have associated concerns, as will be described.

The most common method of determining whether concrete is ready at full strength, involves using standard best practice methods of waiting 28 days, regardless of actual product or environmental conditions. The 28 day wait time method is simply an accepted industry best practices and is not based on actual performance of the concrete in question.

Another method of assessing concrete readiness involves obtaining cylinders of the concrete mix in question and testing each cylindrical sample. This required getting several cylinders and filling them with concrete from same batch. These cylinders are then tested periodically until two cylinders produce the minimum desired compressive strength. The cylinders are only an approximation of the curing of the concrete since they are lab tested and do not exist under the same conditions of the actual concrete project in question.

In prior art methods, determining the cured state of concrete also may be assessed using battery sensors embedded in the concrete. These sensors are calibrated to measure moisture content. The battery sensors are comparatively expensive and have a limited temperature tolerance and lifespan. Battery operated sensors are also bulky and need to be embedded in the concrete, which takes a lot of space, and there is also some concern with how the embedded batteries will impact the strength of the concrete.

Another method that is sometimes applied for determining the moisture content of concrete is by the use of concrete moisture meters. However, these concrete moisture meters only measure the surface moisture content. Since a particular concrete structure could be feet, not inches, deep, measuring only the surface moisture content is not practical or safe in applications in which a sealant or other building material will be installed over the concrete. The surface of the concrete may be bone-dry, but deeper in the concrete form substantial amounts of water may still be present that will need to be released to ensure the strength of the finished product.

Asphalt-laid surfaces frequently show distress which is caused by both movement of traffic over the surface and moisture in the asphalt. The quality of the asphalt mixes, measured by its density, is an important factor to ensure the integrity of the pavement. An improper amount of moisture in an asphalt mixture reduces the asphalt-aggregate bond, which leads to the degradation of the final asphalt product. One possible consequence is what is termed a "tender mix." A tender mix is an internally unstable mix that tends to displace laterally and shove rather than compact under roller loads. Internal mix stability is a function of asphalt binder viscosity and aggregate gradation and shape. Unfortunately, asphalt technologists consider the accurate determination of moisture in an asphalt mixture to be a difficult prospect.

Another industrial process in which moisture is important is that of chemical reactions in which only a small, but precise, amount of water is needed. For example, Diels-Alder reactions work well with a minimal amount of water to neat reactants. In addition, the presence of water will result in an increased reaction rate and formation of a higher purity product. A way to measure moisture content as a large scale process would be valuable. The same is true for all reaction processes that consume water or release water as a by-product.

There is a need for an inexpensive device and method that, in the context of conducting a particular process, can measure moisture content as well as temperature within a viscous mixture in a non-destructive and safe manner. This device should be easy to use so as to provide instant, accurate information on the moisture condition and temperature of the fluid which is utilized in the process. The device ideally will have a long lifespan and capable of withstanding high temperatures. This device should be small and unobtrusive and measure moisture content. This market need is not only for the concrete and asphalt industries, but other commercial or manufacturing endeavors. The foregoing examples were presented for illustrative purposes only, and do not serve to limit the applicability of the devices and methods disclosed in this document.

(2) Description of the Related Art, Including Information Disclosed Under 37 CFR 1.97 and 1.98. The Following Documents Present Methods and/or Devices Related to the Present Inventive Concept U.S. Pat. No. 7,681,438B2; Mar. 23, 2010; Albadri et al; A probe for measuring the hardness of concrete includes a body adapted to receive a retainer such that the combined body and retainer can be held in an aperture extending through a wall of a mould for the hardenable material, with the body extending from the inside of the wall. A sensor circuit includes detector elements supported by the body and disposed when in use in the concrete, and circuit terminals which face the exterior of the mould wall when in use, and are accessible through the retainer for connection to terminals of an external instrument. Preferably, the detector elements are conductive portions of a printed circuit board forming a resonator. The instrument can operate a switch in the probe which interconnects the terminals to indicate a good connection and measures resonator impedance at multiple frequencies.

U.S. Pat. No. 9,032,791B2; May 19, 2015; Duncan, T. An apparatus for measuring humidity or moisture, such as in concrete, is described comprising a sensor module comprising a humidity or moisture sensor in electrical communication with a first set of terminals and a hand-held reader module comprising a controller in electrical communication with a second set of terminals that are mateable with the first set of terminals such that the hand-held reader module is electrically connectable to and electrically disconnectable from the sensor module. The hand-held reader module is configured to read data from the sensor in response to making electrical connection with the sensor module. One set of terminals can comprise plural connector pins and the other set of terminals can comprise plural landing pads, such that the plural connector pins and the plural landing pads make a same electrical connection regardless of the rotational orientation of the hand-held reader module relative to the sensor module.

U.S. Pat. No. 4,186,592; Feb. 5, 1980; Eirich, et al. A method and apparatus for measuring water content of flowable mixtures such as casting sand, concrete, or chemical mixtures. The mixture is agitated in a mixing tray (10), then a moisture sensing measuring probe (7) is inserted into the mix for taking a measurement. The probe is then withdrawn from the mix and cleaned, as by brushing, stripping, blasting with air, or spraying with liquid. A temperature sensor (8) may also be inserted into the mix with the measuring probe. The probe is mounted in a lifting unit (5) which normally holds the probe in a cooling and cleaning casing (6) out of the mix. The unit can also locate the probe at different selected levels within the mix.

U.S. Pat. No. 10,276,015 B2; Apr. 30, 2019; Lang, et al. A method for storing information corresponding to a baled crop during a baling process includes providing a harvesting machine including a control unit, a sensor, and a bale tag reader. The method also includes forming the baled crop with a bale tag by the harvesting machine, identifying the baled crop by the control unit with a bale identifier, and sensing a characteristic of the baled crop by the sensor. The method further includes detecting a bale tag identifier associated with the bale tag by the bale tag reader, communicating the characteristic and bale tag identifier to the control unit, corresponding the characteristic, bale tag identifier and bale identifier of the baled crop to one another, and storing the characteristic, bale tag identifier and bale identifier in an electronic storage unit that is in electrical communication with the control unit.

U.S. Pat. No. 7,398,131 B2; Jul. 8, 2008; Trost, et al; Method and system for controlling and monitoring the quality of concrete based on the concrete's maturity. Various embodiments of the present invention are discussed. First, Enhanced Maturity involves a maturity calibration method to account for the water-to-cementitious-materials ratio, air content, and gross unit weight of the concrete. Second, Moisture-Loss Maturity is a method for determining the appropriate time to terminate moisture-loss protection of concrete and concrete structures. Third, Improved Maturity is a method and system for determining the strength of curing concrete using improved maturity calculations. Fourth, SPC Maturity is a method that beneficially couples maturity measurements and calculations with Statistical Process Control (SPC) methods to enable rapid recognition of changes to the concrete mix and/or incompatibilities between the various components of the concrete mix. Fifth, Loggers, Readers, and Software represent the preferred embodiment for automating and simplifying the implementations of the aforementioned methods.

U.S. Pat. No. 7,231,815 B2; Jun. 19, 2007; Kanare, H. A probe for determining the relative humidity and temperature of a substance such as a concrete floor. The probe is adapted to be inserted into a hole in the substance being tested. The probe has a head portion and a tail portion. A display is provided on the head portion to provide a user with a visual indication of the relative humidity and temperature within the substance. The entire probe structure is designed to be contained within the hole without the need for any components protruding out of the hole to cause an obstruction.

U.S. Published Patent Application #2007/0126433 A1; Jun. 7, 2007; Theophanous, et al.

Non-invasive moisture-sensing within concrete (such as concrete buildings, bridges, etc.) or a polymeric material may be accomplished by a capacitor structure comprising a porous material built inside the concrete or polymeric material. The capacitance measurements change based on the amount of moisture in the porous material. Moisture-sensing can be monitored remotely (including for submerged and other structures), relatively non-invasively, and in a repeatable and reversible fashion without intermediate conditioning or resting.

BRIEF SUMMARY OF THE INVENTION

The inventive concept discloses a method whereby the progress of curing, state of desired hardening, relative viscosity, or maintenance of substance proportions of the internal mass of a viscous substance can be determined and measured electronically at any stage of a specific process. In differing embodiments, the disclosed method measures certain physical properties of the viscous substance, including, but not limited to, moisture content, density, specific gravity, pH, thermal conductivity, electrical conductivity, hardness, strength, and ductility.

The essence of the method is to provide at least one (or in some instances, multiple) small, passive Radio-Frequency Identification (RFID) sensing device that measures moisture, temperature, pH, and/or other parameters of a viscous fluid mixture associated with the various phases of an industrial or manufacturing process. The specific viscous fluid may or may not, undergo gradual change during its maturation into the desired ultimate product. In the preferred embodiment, this inventive concept is intended to monitor curing or drying processes. In such uses, the passive sensing device, (for example, a concrete sensor 12, or a chemical sensor 22) must be embedded within the subject fluid so as to provide ongoing, accurate measurements.

A variety of sensors may be placed at different locations, or utilized for various applications, during a specific process. Each individual sensor is designated with a unique identification code or "tag." The sensor tag 4 would be rewritable and be able to provide key data concerning the pertinent process, such as date, time and/or location of creation, or date of expiration, etc.

Whenever the sensor is read, the key information is immediately displayed. The operating temperature range of the sensor must be functional from below freezing to above boiling. An interrogator 33 is used to read and wirelessly transmit the moisture content, temperature, and/or pH data given by the sensor 12, 22. The interrogator 33 sends the data to a specific software application or other program which will be populated with the algorithm(s). This data will then be converted to a useable format.

In the preferred embodiment, the sensor 12, 22 is the size of a business card, however, sizes may vary, dependent upon the state of the technology used and the capabilities of the interrogator 33.

BRIEF DESCRIPTION OF THE VIEWS OF DRAWINGS AS EXEMPLARY EMBODIMENTS OF THE INVENTIVE CONCEPT

FIG. 2B further shows the asphalt base layer 18, the aggregate layer 19, and the soil sub-grade 20.

DETAILED DESCRIPTION OF THE INVENTION

The objects, features, and advantages of the inventive concept presented in this application are more readily understood when referring to the accompanying drawings. The drawings, totaling fourteen figures, show the basic components and functions of embodiments and/or methods of use. In the several figures, like reference numbers are used in each figure to correspond to the same component as may be depicted in other figures.

Figure 1A:
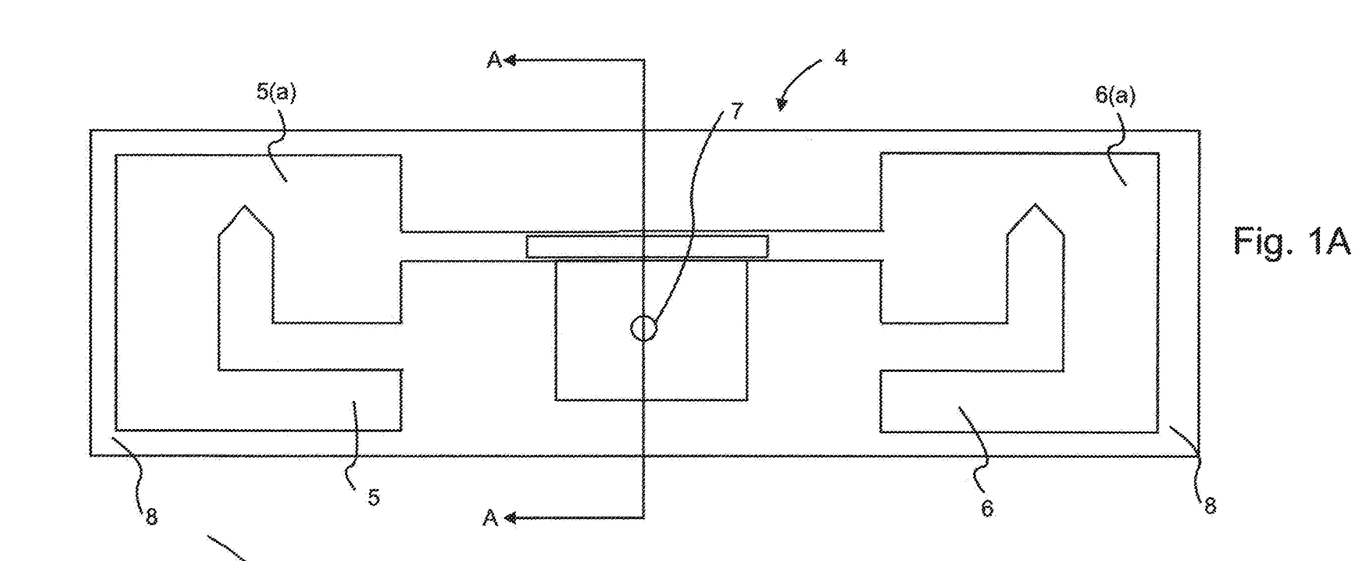
FIG. 1A is a drawing of a typical sensor 4, showing the sensor pickup area 7 for measurement of a specific property of a viscous substance, along with the left and right antenna sections 5, 6.

The discussion of the present inventive concept will be initiated with FIG. 1A. In FIG. 1A there is illustrated a plan view of a typical electronic sensor 4, further equipped with a "tag." The tag pickup area 7 is utilized for measurement of a specific property of a viscous fluid 40 (not shown), while the left and right antenna sections 5, 6 are shown integral to the left antenna base 5(a) and right antenna base 6(a). The tag device measures moisture, temperature, pH, or other process parameters, that would be essential to maintenance or completion of a finished product.

Figure 1B:
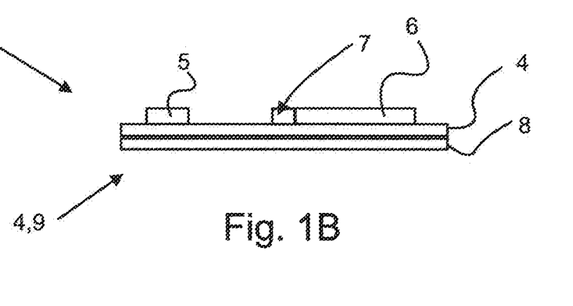
FIG. 1B illustrates a side view 9 of the sensor 4 of FIG. 1A, as seen from the perspective of section line A-A.

FIG. 1B illustrates a side view 9 of the sensor 4 and further shows an adhesive backing 8 which backing 8 normally comes as standard configuration for off-the-shelf sensors 4 of this type. The sensor 4, in conjunction with a tag, acquires information on the properties of a viscous fluid, or other substance in which the sensor 4 immersed. This information is stored electronically within the tag until electronically interrogated by a compatible device which emits interrogating radio waves. The interrogating device (not shown) is essentially a small, passive Radio Frequency Identification (RFID) emitter that may be mobile or at a stationary location. The information may also be transmitted by conventional electronic communication via a land-line or similar hard-wired connection.

In the preferred embodiment the sensor 4 is passive. Other embodiments of this inventive concept may be equipped with battery-powered, or locally-powered sensors 4. These are generally known as "active" tags and may operate at hundreds of meters from an RFID reader.

Figures 2, 2A, 2B:
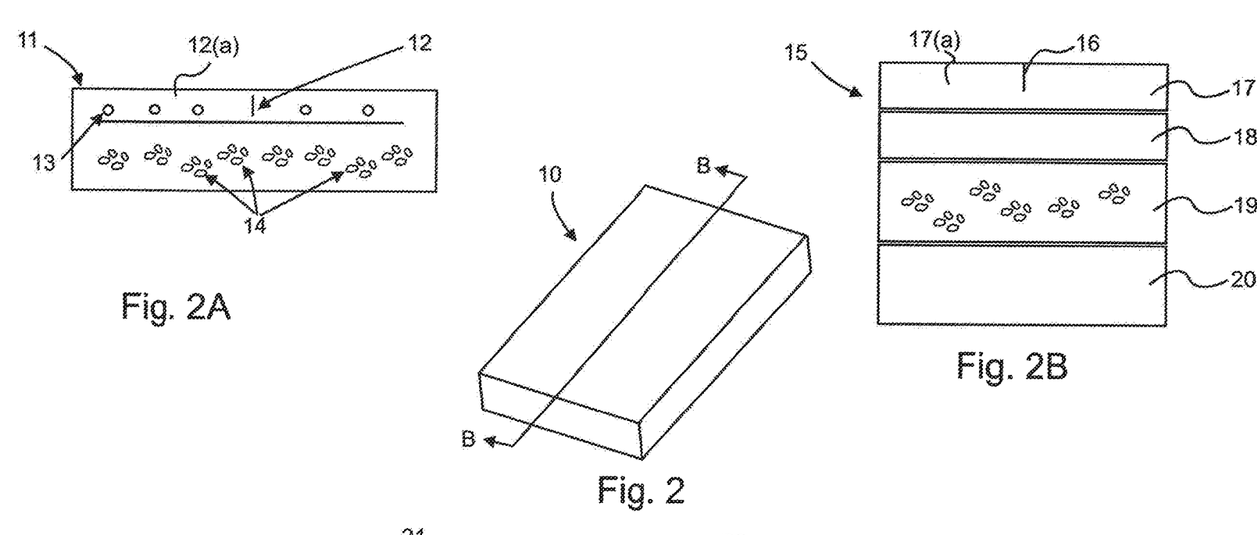
FIG. 2 illustrates a stylized cutout of a block section 10 of any of a variety of specific materials, further showing the cross-sectional direction of view of the section 10.
FIG. 2A presents a cross-sectional view of a hypothetical section of concrete 11, as would be seen from section line B-B, further showing a generic sensor 12 (sensor specific to concrete) embedded within.
FIG. 2B shows a cross-sectional view of a section of asphalt 15 with a sensor 16 specific to asphalt embedded near the top surface 17.

In FIG. 2 there is illustrated a hypothetical block of any of a variety of materials 10. Section line B-B, depicts the orientation of a cross-sectional view of any one of different varieties of the block material 10. FIG. 2A specifically represents a cross-sectional view of concrete block material 11. A specific concrete sensor 12, essentially functioning in the same manner as sensors 4 previously described, is embedded near the concrete outer surface 12(a). The concrete rebar 13, along with aggregate 14 typically found in concrete structures is also shown.

In FIG. 2B there is illustrated a cross-sectional view (an approximation of the view from cross-section line B-B) of a block of asphalt 15. A specific asphalt sensor 16, along with a tag 16(*a*), functions in the same manner as the sensor 4 previously described. The asphalt sensor 16 is embedded near the surface 17(*a*) of the asphalt layer 17, directly above the asphalt base layer 18. The asphalt aggregate layer 19 and the soil subgrade 20 are further shown.

Figure 2C:
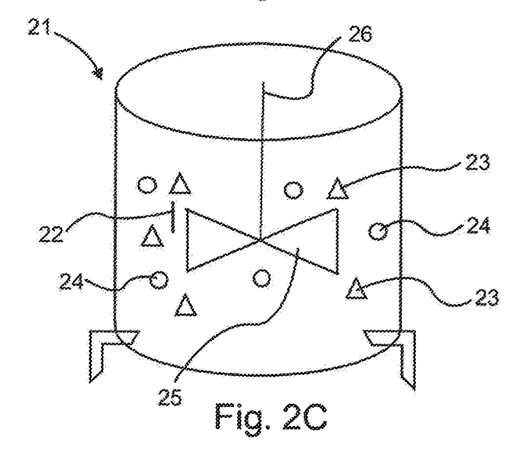
FIG. 2C presents a stylized view of the interior of a chemical mixing, or reactive, tank 21. Also shown is a sensor 22 embedded with other mix components, these components typically a first chemical agent 23, a second chemical agent 24. Stylized mixing blades, are represented by item 25.

FIG. 2C depicts a stylized view of the interior of a chemical mixing, or reaction, tank 21. A sensor 22, along with its associated tag 22(*a*) (not shown) is embedded within chemical components, which by way of illustration only, comprise a first chemical 23 and a second chemical 24. Both chemicals 23, 24 are conceivably mixed with other necessary components. FIG. 2C, thus depicts representations of the various constituents that may be included in a mixing/reactive tank 21. Further shown is a mixing blade 25 and a blade axis 26 integral to the reaction tank 21.

Figure 3:
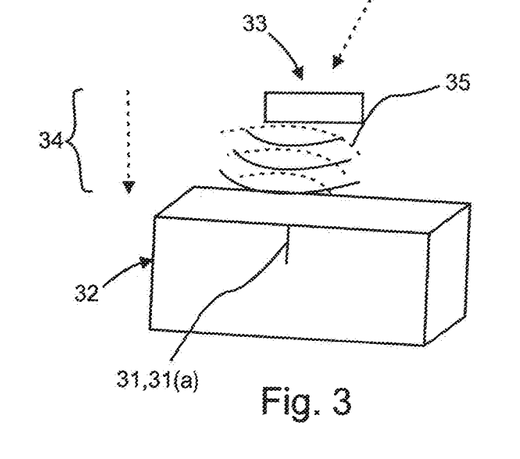
FIG. 3 depicts the flow of the process of reading the information acquired by a tag 31(a) attached to a sensor 31 embedded within a container 32 of viscous fluid mixture. The information is garnered by an interrogator 33 and transmitted to an internet-based "Cloud" 37 data storage system.

FIG. 3 depicts the process of reading the information acquired by a tag 31(*a*) attached to a sensor 31 embedded within a container 32 of viscous fluid mixture. The sensor 31 and its tag 31(*a*), when electronically prompted, picks up data from the changing parameters of the viscous fluid in which it is embedded, the data being in a readily useable form for electronic transmission. An electronic interrogator 33 either automatically, or upon manual actuation, generates electromagnetic radio waves 34 to empower the sensor's tag 31(*a*). Thus, the interrogator 33 provides minute amounts of power 34 to the sensor 31 and the tag 31(*a*) shown as FIG. 3. The sensor 31, upon receiving power from the interrogator 33, reads the current conditions of the process and has enough power to send the signal back to the interrogator 33. The interrogator 33 then stores and sends the data wirelessly to a storage location, typically to a Cloud 37 location. In some embodiments, the current conditions of the process may be transmitted by conventional electronic communication via a land-line or similar hard-wired connections.

In FIG. 3, the depicted sensor 31 functions in the same manner as described earlier for typical sensors 4 of this type, and is embedded in the container 32 of viscous fluid. The viscous fluid could be, by way of illustration, and not limitation, concrete, asphalt, chemical reactants, or other manufacturing or industrial substances. One common characteristic of such viscous fluids is that water, or moisture content, plays a key variable in any curing or manufacturing process. The passive sensor 31 receives electrical power from the interrogator 33 and implements readings of physical properties of the viscous substance, including, but not limited to, moisture, temperature, pH or substance parameters. The sensor 31 then transmits, by radio wave 35, its readings back to the interrogator 33, shown in FIG. 3 as an arrow and broken curvilinear waves.

Figure 3A:
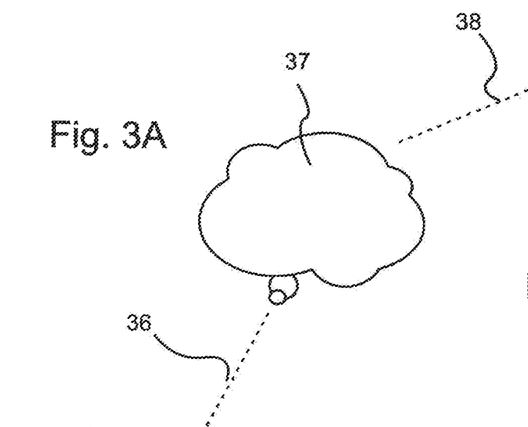
FIG. 3A is a stylized presentation of the Cloud 37 which stores, processes, and provides access to the corresponding algorithms 38.

With the unique tag 31(*a*) of the sensor 31, precise readings can be correlated to the location of the sensor 31 within the viscous fluid, or perhaps the unique individual tags of multiple sensors within the fluid. The interrogator 33 may temporarily store, or transmit 36 the readings received from the sensor 31 to a cloud 37 data storage system, as shown in FIG. 3A. The data stored in the cloud 37 is maintained and made available, accessible, and interpretable by means of various algorithms 38.

Figures 3B, 3C, 3D:
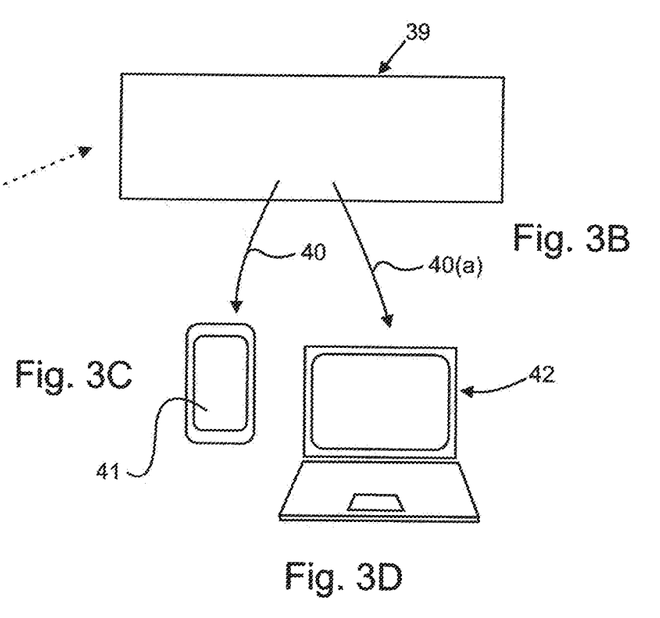
FIG. 3B represents the electronic consolidation 39 of a variety of algorithms and transmittal to final users.
FIG. 3C depicts a mobile phone or device 41 for reception of the algorithmic information.
FIG. 3D illustrates a desktop computer 42 for reception of the algorithmic information.
Figures 4, 4A:
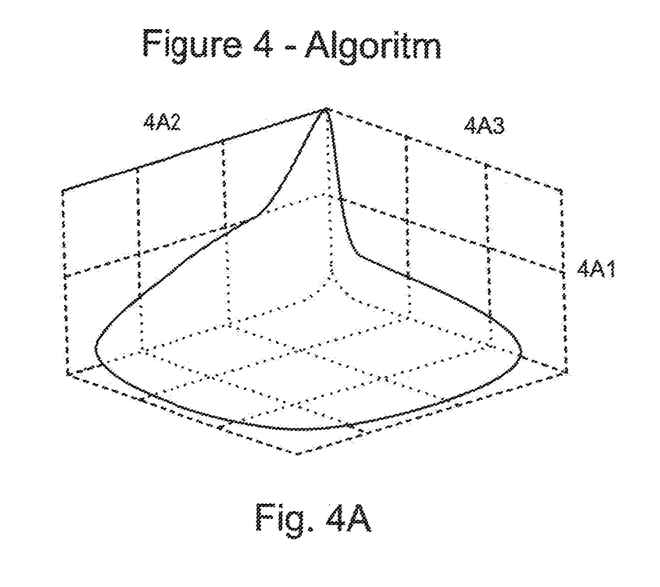
FIG. 4A and FIG. 4B show stylized, three-dimensional representations of algorithms that track the variables of temperature, moisture, and pH factor during stages of a process involved with acquiring hardness, or compressive strength, of a specific viscous fluid.
Figure 4B:
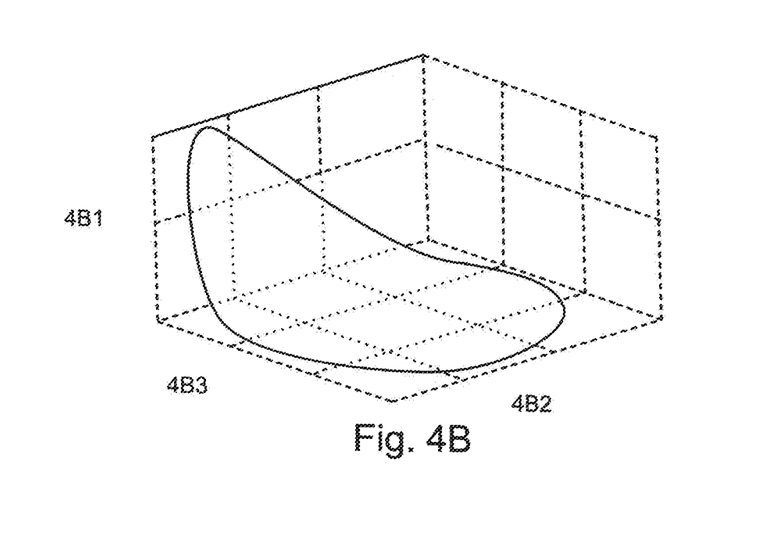

A specific algorithm or algorithms 38 translates the data given by the sensor 33 into a useable form depending on the specific process which takes place. FIG. 3B is a representation of the collection and consolidation of specific algorithm 39 generated by means of the immediately preceding examples. As is expected, for accuracy in assessing the attainment of a substance phase for specific processes, it is essential that different algorithms 38 be utilized for instance, with different grades of concrete (2000 psi, 2500 psi, 3000 psi, etc). Further, different algorithms 38 must be computed for the differing grades of asphalt (I-2, I-4, I-5, etc.). It is necessary that custom-designed/calculated algorithms 38 be calculated for other specific processes. FIG. 4A and FIG. 4B provide information on the function of certain algorithms 38 for assessment of each phase or phases of completion of a process.

Once the data is collected in the Cloud 37 data storage system and the appropriate algorithm 38 translates 39 the collected data, the information is sent to a final user or users (not shown) via appropriate communications means 40 and 40(*a*). Ultimate end users may acquire the transmitted data 39 by means of mobile phones 41 and desktop computers 42, respectively, shown in FIG. 3C and FIG. 3D.

In FIG. 4 (comprising FIG. 4A and FIG. 4B) there is shown a three-dimensional, pictorial representations of algorithms correlating moisture, temperature, and/or pH to the relative percentage of completion of a process to achieve hardness, or compressive strength. FIG. 4A relates low moisture and low temperature or pH to a high percentage completion of the process. Percentage completion of the process is represented by 4A1, with 4A2 being moisture content, and 4A3 is temperature.

FIG. 4B relates high moisture and low temperature or pH to high percentage complete process. Item 4B1 is percentage completion of the process, 4B2 is moisture content, and 4B3 is temperature. Each application in which a sensor will be used to determine the percentage completion of the process will have its own unique algorithm developed.

A data collection period will be used for collection of results of temperature, moisture, and pH readings over specific times under varying conditions. The resultant rendering of the hardness and strength, or possibly a curing objective 97 of the substance can then be precisely indicated. All the data collected will be plotted until algorithmic graphs are created, as demonstrated with FIG. 4A and FIG. 4B. As an example, assuming concrete slurry is the substance, in FIG. 4B, all moisture readings are on the X-axis represented by axis 4B2. When there is low moisture in concrete, it is expected that the PSI strength of concrete is high. The PSI (or percentage of finished curing process) is in the Z-direction of the 3-dimensional graph, represented by axis 4B1. On the Y-Axis is temperature, represented by axis 4B3.

In FIG. 4B, the plot, "4B2" is the moisture content axis. At the far left is very low moisture and the far right is very wet. If there were presented a scale from 0.0% to 100.0% moisture, then perhaps in a concrete application, this would translate to a correlated scale of 1.0% to about 15.0% moisture. The most practical utilization of the disclosed inventive concept is to focus on the key parameters in critical ranges, for instance, 0.0% to 30.0% range instead of 0.0% to 100.0% moisture.

In FIG. 4B, "4B3" represents temperature axis. To the left is low temperature and to the right is high temperature. The temperature range, in Celsius, is between 10.0 and 35.0 degrees. The customarily-designated Z-axis 4B1 depicts the strength of concrete in PSI. Higher readings oin the Z-axis 4B1 translates to higher strength while lower readings in the Z-axis 4B1 represent lower levels of strength. Basically, when the temperature is close to ambient (when concrete is poured it gets hot) and moisture content is low, the current strength of the concrete batch will be high.

Again, using concrete as the representative substance, when the temperature may be high, there is still curing time left. Only when the moisture content is low and temperature is also relatively low, will the curing of the concrete be complete. Therefore, the moisture reading and temperature, once known, can be plotted and compared to previous data to determine the third variable, the compressive strength of concrete, which would be representative of the percentage of a complete curing process of concrete. Compressive strength could be in pounds per square inch, (psi) or it could be in Newtons per square millimeter ($N/mm^2$).

Figure 5:
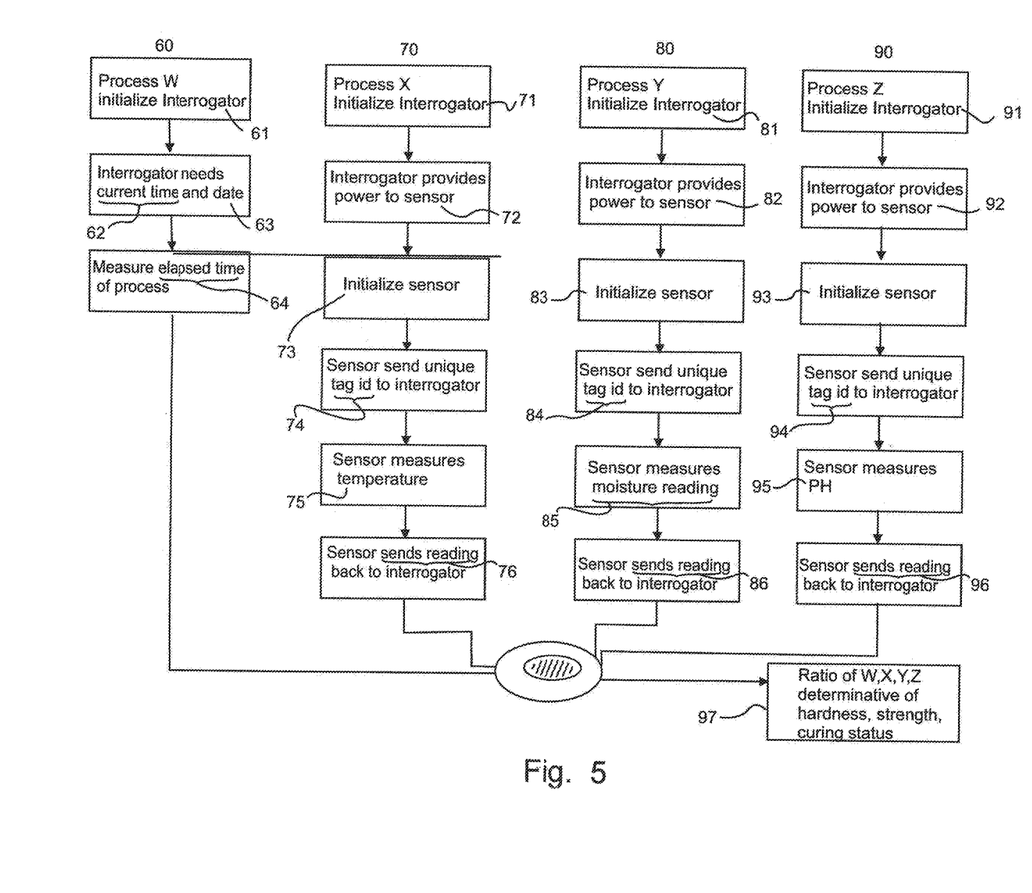
FIG. 5 presents an integrated flow chart depicting the various process steps necessary for accomplishing a desired condition of particular viscous fluid.

FIG. 5 presents an integrated flow chart depicting the various process steps 60, 70, 80, 90, necessary for accomplishing a desired condition of particular viscous fluid. At process W 60, an interrogator 61 initiates the current time 62 and date 63 and maintains a continuous tracking of elapsed time 64. At process X 70 an interrogator 71 provides power to the applicable sensor 72, which sensor 72 sends its unique tag ID 74, and its reading 76 of temperature 75 back to the interrogator 71.

At process 80 an interrogator 81 provides power to the applicable sensor 82, which sensor 82 sends both its unique tag ID 84, and the reading 86 of moisture content 85 back to the interrogator 81. At process 90 an interrogator 91 provides power to the applicable sensor 92, which sensor 92 sends its unique tag ID 94, and its reading 96 of pH 79 back to the interrogator 91.

The culmination and ratios of the above-described processes 60, 70, 80, and 90 all render a cumulative determination of the strength and hardness 97 of the viscous fluid which is being processed.

The user(s), upon the receipt of usable moisture and related data such as temperature, pH, or other parameters, can then accurately determine the stage of the process being monitored. Over a period of time, when the appropriate stage or completion percentage 97 of a process is determined, the user can make better decisions about the specific process, without additional testing or other complicated, inefficient attempts at guessing.

While preferred embodiments of the present inventive method have been shown and disclosed herein, it will be obvious to those persons skilled in the art that such embodiments are presented by way of example only, and not as a limitation to the scope of the inventive concept. Numerous variations, changes, and substitutions may occur or be suggested to those skilled in the art without departing from the intent, scope, and totality of this inventive concept. Such variations, changes, and substitutions may involve other features which are already known per se and which may be used instead of, in combination with, or in addition to features already disclosed herein. Accordingly, it is intended that this inventive concept be inclusive of such variations, changes, and substitutions, as described by the scope of the claims presented herein.

What is claimed is:

1. A method for determination, at any point in time, a quality or phase of a specific physical property of a viscous substance, as the viscous substance progresses through stages of a particular process, the method comprising:
   (a) preparing algorithms of compilations of stored data corresponding to historic data showing effects of temperature, time, moisture content, pH, and other variable conditions on the physical properties of the viscous substance;
   (b) positioning the viscous substance within or upon a specific container or enclosure;
   (c) embedding sensors in an interior mass of the viscous substance;
   (d) obtaining periodic measurements, transmitted from the sensors, of the specific physical properties of the viscous substance, in sequential segments of time;
   (e) accessing the algorithms for direct comparison with the periodic measurements obtained from the sensors and thereby converting the obtained periodic measurements into a rendering of a stage, or quality, of the specific physical property of the viscous substance;
   (f) transmitting the rendering of the quality of the specific physical property of the viscous substance to a mobile phone, electronic storage device, or desktop computer of an end user.

2. The method of claim 1, wherein the viscous substance is a concrete slurry.

3. The method of claim 1, wherein the viscous substance is asphalt.

4. The method of claim 1, wherein the viscous substance is being transported through a pipeline or conduit.

5. A method for determination, at any point in time, a quality or phase of a specific physical property of a viscous substance, as the viscous substance progresses through a particular process, the method comprising:
   (a) preparing algorithms of compilations of stored data corresponding to historic data showing effects of temperature, time, moisture content, pH, and other variable conditions on the physical properties of the viscous substance;
   (b) providing (i) a container or defined volume of the viscous substance, (ii) a plurality of sensors having electronic tag identifiers, (iii) access to a cloud data storage system, and (iv) at least one interrogator;
   (c) embedding the sensors within an interior mass of the viscous substance;
   (d) obtaining periodic measurements, as transmitted from the sensors to the interrogator, of the specific physical property or properties of the viscous substance;
   (e) accessing the algorithms for direct comparison with the periodic measurements obtained from the sensors;
   (f) converting the obtained periodic measurements into a rendering of a stage, or quality, of the specific physical property of the viscous substance;
   (g) transmitting the rendering of the quality of the specific physical property of the viscous substance to a mobile phone, electronic storage device, or desktop computer of an end user.

6. The method of claim 5, wherein the viscous substance is a concrete slurry.

7. The method of claim 5, wherein the viscous substance is asphalt.

8. The method of claim 5, wherein the viscous substance is being transported through a pipeline or conduit.

9. The method of claim 5, wherein the periodic measurements of the viscous substance are stored in a data server located remotely from the interrogator.

10. The method of claim 5, wherein the transmitting of the rendering of the quality of the specific physical property of the viscous substance is by conventional electronic communication via a hard-wired connection.

11. The method of claim 5, wherein the transmitting of the rendering of the quality of the specific physical property of the viscous substance is stored within the interrogator and intermittently wirelessly sent to a Cloud storage location.

12. A method for determination, at any point in time, a viscous substance's degree of hardness or compressive strength as the viscous substance progresses through stages of a curing process, the method comprising:

(a) preparing algorithms of compilations of stored data corresponding to historic data showing effects of temperature, time, moisture content, pH, and other variable conditions on physical properties of the viscous substance;

(b) providing (i) a container or defined volume of the viscous substance, (ii) a plurality of sensors having electronic tag identifiers, (iii) access to a cloud data storage system, and (iv) at least one interrogator;

(c) inserting a certain number of the plurality of sensors into the viscous substance;

(d) initiating an electronic time-keeping mechanism;

(e) powering at least one interrogator to receive readings of a multiplicity of the physical properties of an internal mass of the viscous substance, as transmitted by the sensors;

(f) communicating, by means of the interrogator, the readings of the physical properties of the viscous substance for storage within an electronic cloud-based network;

(g) converting, using the historic data contained in the algorithms, the readings into a relative hardness or percentage of completion of the curing process; and (h) transmitting the relative hardness or percentage of completion of the curing process to mobile phones, devices, or desktop computers of ultimate users.

13. The method of claim 12, wherein the viscous substance is a concrete slurry.

14. The method of claim 12, wherein the viscous substance is asphalt.

15. The method of claim 12, wherein the readings of the physical properties of the viscous substance are stored within the interrogator.

16. The method of claim 12, wherein the physical properties of the viscous substance are stored in a data server located remotely from the interrogator.

17. The method of claim 12, wherein the transmitting of the relative hardness or percentage of completion of the curing process is transmitted by conventional electronic communication via a hard-wired connection.

18. The method of claim 12, wherein the transmitting of the relative hardness or percentage of completion of the curing process is stored within the interrogator and intermittently wirelessly sent to a Cloud storage location.

19. The method of claim 12, further comprising storing the physical properties of the viscous substance in a data matrix, the data matrix including a plurality of columns for the physical properties sensed at a variety of locations within the viscous substance.

* * * * *